(12) United States Patent
Mu et al.

(10) Patent No.: US 10,650,914 B2
(45) Date of Patent: May 12, 2020

(54) FRESH WATER ACUTE CRITERIA PREDICTION METHOD BASED ON QUANTITATIVE STRUCTURE-ACTIVITY RELATIONSHIP FOR METALS

(71) Applicant: Chinese Research Academy of Environmental Sciences, Beijing (CN)

(72) Inventors: Yunsong Mu, Beijing (CN); Fengchang Wu, Beijing (CN); Haiqing Liao, Beijing (CN); Yingchen Bai, Beijing (CN); Xiaoli Zhao, Beijing (CN); Ying Wang, Beijing (CN)

( * ) Notice: Subject to any disclaimer, the term of this patent is extended or adjusted under 35 U.S.C. 154(b) by 271 days.

(21) Appl. No.: 15/659,608

(22) Filed: Jul. 25, 2017

(65) Prior Publication Data

US 2017/0323085 A1   Nov. 9, 2017

Related U.S. Application Data

(63) Continuation of application No. PCT/CN2015/080631, filed on Jun. 3, 2015.

(30) Foreign Application Priority Data

May 13, 2015   (CN) .......................... 2015 1 0240546

(51) Int. Cl.
   *G06F 17/18*      (2006.01)
   *G06F 19/00*      (2018.01)
   (Continued)

(52) U.S. Cl.
   CPC ............. *G16C 20/30* (2019.02); *G06F 17/18* (2013.01); *G06Q 10/04* (2013.01); *G06Q 50/26* (2013.01); *G16B 99/00* (2019.02)

(58) Field of Classification Search
   USPC ........................................ 702/2, 19, 23, 179
   See application file for complete search history.

(56) References Cited

U.S. PATENT DOCUMENTS

2005/0085626 A1   4/2005  Leung et al.
2011/0098933 A1*  4/2011  Ochs ................. A61B 5/14551
                                                                 702/19
(Continued)

FOREIGN PATENT DOCUMENTS

CN   103646180 A  *  11/2013
CN   103577714 A      2/2014
CN   103646180 A      3/2014

OTHER PUBLICATIONS

Chen, C. et al., "Derivation of marine water quality criteria for metals based on a novel QICAR-SSD model," Environ Sci Pollut Res, Oct. 2014, pp. 4297-4304.*

(Continued)

*Primary Examiner* — Alexander Satanovsky
*Assistant Examiner* — Jeffrey P Aiello
(74) *Attorney, Agent, or Firm* — W&K IP

(57) ABSTRACT

The present invention relates to a fresh water acute criteria prediction method based on a quantitative structure-activity relationship for metals. An unknown toxic endpoint of a metal is predicted according to a quantitative relationship between structural characteristics of heavy metal ions and acute toxicity effects of aquatic organisms, and hazard concentrations for protecting the aquatic organisms of different proportions are derived from sensitivity distribution analysis on different species. The fresh water acute criteria prediction method is a method for establishing a metal toxicity predictive model by integrating physicochemical structural parameters of heavy metals and toxic mechanisms of different aquatic organisms and applying the metal toxicity predictive model to prediction of an unknown criteria reference value.

10 Claims, 4 Drawing Sheets

(51) Int. Cl.
*G06F 19/10* (2011.01)
*G16C 20/30* (2019.01)
*G16B 99/00* (2019.01)
*G06Q 10/04* (2012.01)
*G06Q 50/26* (2012.01)

(56) References Cited

U.S. PATENT DOCUMENTS

| | | | |
|---|---|---|---|
| 2013/0238252 A1* | 9/2013 | Perenon | H01J 49/0018 |
| | | | 702/23 |
| 2014/0107975 A1* | 4/2014 | Manton | G01D 3/10 |
| | | | 702/179 |
| 2014/0134745 A1* | 5/2014 | Peterson | G01N 33/46 |
| | | | 436/93 |
| 2015/0178415 A1* | 6/2015 | Sano | B21B 37/00 |
| | | | 700/207 |
| 2015/0212235 A1* | 7/2015 | Barwise | G06F 17/18 |
| | | | 703/2 |
| 2015/0220488 A1* | 8/2015 | Healy | G06F 17/18 |
| | | | 702/181 |
| 2015/0240315 A1* | 8/2015 | Blakemore | C12Q 1/6834 |
| | | | 514/265.1 |
| 2015/0254382 A1* | 9/2015 | Bolander | G06F 17/5018 |
| | | | 703/2 |

OTHER PUBLICATIONS

Cheng Chen et al., "Derivation of Marine Water Quality Criteria for Metals Based on a Novel QICAR-SSD Model", Environmental Science and Pollution Research, vol. 22, No. 6, Mar. 31, 2015.

* cited by examiner

FRESH WATER ACUTE CRITERIA PREDICTION METHOD BASED ON QUANTITATIVE STRUCTURE-ACTIVITY RELATIONSHIP FOR METALS

CROSS-REFERENCE TO RELATED APPLICATIONS

This application is a continuation of International Patent Application No. PCT/CN2015/080631 with a filing date of Jun. 3, 2015, designating the United States, now pending, and further claims priority to Chinese Patent Application No. 201510240546.9 with a filing date of May 13, 2015. The content of the aforementioned applications, including any intervening amendments thereto, are incorporated herein by reference.

TECHNICAL FIELD

The present invention relates to the field of fresh water quality criteria models and particularly relates to a fresh water acute criteria prediction method based on a quantitative structure-activity relationship for metals.

BACKGROUND OF THE PRESENT INVENTION

Metal contamination is one of the most challenging environmental problems of the present century. Excessive heavy metals enter into a natural environment to destruct biological diversity and cause harmful influences on an ecological environment and human health. To formulate scientific environmental criteria for metals is a basis of environmental protection and risk assessment. America is a country which internationally develops criteria study first, while an existing criteria system in China mainly copies or draws on foreign achievements and lacks of science. In the latest criteria documents, 15 metals are listed in a directory of precedence-controlled pollutants and non-precedence-controlled pollutants, while only 10 metals have criteria reference values. Water quality criteria values of most of metals are lost, for a primary reason of insufficient biological toxicity data deficiency and a secondary reason of influence by environmental elements. Only criteria research of metals such as copper, nickel is deep. At present, standardized biological toxicity testing is the only way for obtaining a criteria value currently. However, because the heavy metals have wide varieties and complicated structures and forms, manpower, material resources and financial resources need to be consumed during lots of toxicity tests for criteria derivation, and a metal form in a complex biological system is difficult to be accurately measured. Development of heavy metal water quality criteria research is hindered. Although various toxic endpoints are predicted by researchers by virtue of calculation means, a real means for toxicity and water quality criteria prediction is not reported. The development does not depend on a criteria prediction method of testing measurement and conforms to national conditions of China, thereby saving lots of manpower, material resources and financial resources.

A quantitative structure-activity relationship (QSAR) method looks for an inner link between structures and biological activities of targeted pollutants by adopting a statistical analysis means and is widely applied to prediction and evaluation of various toxic effects as an effective means of toxic mechanism researches. The QSAR method is not limited by experimental conditions and testing instruments, and the biological activities of the pollutants are researched and predicted by adopting various computational chemistry and data mining technologies, so the QSAR method has particularly obvious advantages while confronting with batches of pollutants and multiple tested species and has unique charm in aspects of toxicity prediction and risk evaluation. As is known to all, an ionic form is the most active form of metals, and biological activities of dissolved metals are closely related to free ion concentrations. The researchers try to carry out a QSAR research of metal ions in an ideal system and propose a method for predicting the biological activities of the ions based on a quantitative ion characteristic-activity relationship. Newman et al. establish a QSAR equation by utilizing toxicity testing data of marine luminous bacteria (*V. fischen*) and predict metal toxicity. The result shows that a first hydrolysis constant |log $K_{OH}$| and the metal ions have a strong interaction relationship on the toxic effects of organisms. Bogaerts et al. indicate that a metal ion soft index σp is an optimal modeling parameter of the toxicity prediction equation while evaluating the interaction relationship between a toxic effect of protozoa (*T. pyriformis*) and physicochemical characteristics of the metal ions.

The methods above are one-parameter predictive models based on a single species and lack of systematic toxicity prediction and analysis of multiple species in the ecological system, and prediction capabilities and application domains of the models are very limited.

In view of the defects above, the present invention is obtained by the inventor of the present invention through long-term research and practice.

SUMMARY OF PRESENT INVENTION

The purpose of the present invention is to provide a fresh water acute criteria prediction method based on a quantitative structure-activity relationship for metals, in order to overcome the technical defects above.

In order to achieve the purpose above, the present invention provides the fresh water acute criteria prediction method based on the quantitative structure-activity relationship for metals. An unknown toxic endpoint of a metal is predicted according to a quantitative relationship between structural characteristics of heavy metal ions and acute toxicity effects of aquatic organisms, and hazard concentrations for protecting the aquatic organisms of different proportions are derived from sensitivity distribution analysis on different species.

A specific process is as follows:

step a, acquiring, screening, calculating and summarizing modeling toxicity data;

step b, screening five-phylum and eight-family aquatic model organisms;

step c, building a data set of metal ion structural descriptors, and performing linear regression analysis between each structural parameter as an independent variable and toxic endpoints, to obtain structural descriptors in the top two by virtue of correlation coefficient sorting structural descriptor;

step d, building a toxicity predictive model and performing a robustness test, establishing a multiple regression equation, estimating parameters, and inspecting by adopting a value P corresponding to statistic F;

step e, performing internal validation on a quantitative structure-activity relationship (QSAR) model;

step f, calculating an application domain of the model; and for a calibrated model, drawing a leverage vs residuals diagram by taking a leverage value h as a horizontal ordinate and taking a standardized residual of each data point as a vertical ordinate; and step g, rapidly screening and predicting the unknown toxicity of a metal and a criteria value by adopting the obtained toxicity prediction value and species sensitivity analysis.

Further, in the step c above, linear regression analysis is performed by taking a toxic endpoint of a single species as a dependent variable and taking the structural parameter corresponding to each metal as the independent variable, and a correlation coefficient r is calculated according to the following formula (1):

$$r = \frac{\sum_{i=1}^{n}(x_i - \bar{x})(y_i - \bar{y})}{\sum_{j=1}^{n}(x_i - \bar{x})^2(y_i - \bar{y})^2} \quad (1)$$

in the formula, $\bar{x}$ and $\bar{y}$ respectively represent the means of each structural parameter and the toxicity value, and $x_i$ and $y_i$ respectively represent a structural parameter and a toxicity value of the ith metal.

The correlation coefficient $r>0.8$ is a significant correlation parameter.

Further, in the step c above, the built metal ion structural descriptor set comprises a soft index $\sigma p$, a maximum stability constant $\log\text{-}\beta_n$ of complexes, Pauling electronegativity $X_m$, a covalent index $X_m^2 r$, an atom ionization potential $AN/\Delta IP$, a first hydrolysis constant $|\log K_{OH}|$, an electrochemical potential $\Delta E_0$, an atomic size $AR/AW$, polarizable force parameters $Z/r$, $Z/r^2$ and $Z^2/r$ and quasi polarizable force parameters $Z/AR$ and $Z/AR^2$.

Further, the process of the step d is as follows:

step d1, building the multiple regression equation and performing parameter estimation;

a quantitative ion characteristic-activity correlation equation $Y=XB+E$ of each model organism is constructed by taking two optimal structural parameters determined in the step d above as the independent variable X and taking a metal activity value as the dependent variable Y through a multiple linear regression analysis method; and a formula (2) below can be referred to, wherein $$Y = \begin{pmatrix} y_1 \\ y_2 \\ \vdots \\ y_n \end{pmatrix}, \quad X = \begin{pmatrix} 1 & x_{11} & x_{12} \\ 1 & x_{21} & x_{22} \\ \vdots & \vdots & \vdots \\ 1 & x_{n1} & x_{n2} \end{pmatrix}, \quad B = \begin{pmatrix} \beta_0 \\ \beta_1 \\ \beta_2 \end{pmatrix}, \quad E = \begin{pmatrix} \varepsilon_1 \\ \varepsilon_2 \\ \vdots \\ \varepsilon_n \end{pmatrix} \quad (2)$$

n is the number of observed values, B is a regression coefficient matrix, and E is a random error matrix.

Parameters in the equation are estimated by a least square method, and X' is a transposed matrix of X:

$$\hat{B} = \begin{pmatrix} \hat{\beta}_0 \\ \hat{\beta}_1 \\ \dots \\ \hat{\beta}_m \end{pmatrix} = (X'X)^{-1}X'Y \quad (3)$$

step d2, inspecting goodness of fit and inspecting significance of the regression equation by adopting F;

a testing index of goodness of fit of the model refers to: square $R^2$ of the correlation coefficient, a degree-of-freedom corrected correlation coefficient $\overline{R}^2$, and a standard deviation RMSE;

indexes of F-testing refer to the value F and correlative probability p calculated by Multi-ANOVA; and testing is preformed by adopting the value P corresponding to the statistic F;

step d3, obtaining a judgment standard: according to a toxicity data acquisition way, in-vitro experiment $R^2$ is more than or equal to 0.81, in-vivo experiment $R^2$ is more than or equal to 0.64; a significance level is $\alpha$, and when p is less than $\alpha$, the regression equation is significant.

Further, the step d3 above is calculated according to the following formulas:

$$R^2 = 1 - \frac{\sum_{i=1}^{n}(y_i - \hat{y})^2}{\sum_{i=1}^{n}(y_i - \bar{y})^2} \quad (4)$$

$$\overline{R}^2 = 1 - (1 - R^2)\frac{n-1}{n-3}$$

$$RMSE = \sqrt{\frac{\sum_{i=1}^{n}(y_i - \hat{y})^2}{n-3}} \quad (5)$$

$$F = \frac{[SS(\text{total}) - SS(\text{residual})]/2}{SS(\text{residual})/(n-3)} = \frac{\left[\sum_{i=1}^{n}(y_i - \bar{y})^2 - \sum_{i=1}^{n}(y_i - \hat{y})^2\right](n-3)}{2 \times \sum_{i=1}^{n}(y_i - y)^2} \quad (6)$$

In the formulas, $\hat{y}$ represents a predicted toxicity value of the ith metal, $R^2$ represents the square of the correlation coefficient, $\overline{R}^2$ represents the degree-of-freedom corrected correlation coefficient, and RMSE represents the standard deviation.

Further, the specific process of the step e above is as follows:

step e1, selecting most of samples for modeling in given modeling samples, reserving a small part of samples for predicting by using the established model, and calculating prediction errors of the small part of samples;

step e2, recording the sum of squares of the prediction errors in all the equations until all the samples are predicted once only;

step e3, calculating a cross-validation correlation coefficient $Q^2_{cv}$ and a cross-validation root-mean-square error $RMSE_{CV}$, wherein a discrimination basis is as follows: $Q^2_{cv}>0.6$ and $R^2-Q^2_{cv}\leq 0.3$.

Further, calculation formulas adopted in the step e3 above are as follows:

$$Q^2_{CV} = 1 - \frac{\sum_{i=1}^{n}\left(y_i^{obs} - y_i^{predcv}\right)^2}{\sum_{i=1}^{n}\left(y_i^{obs} - \bar{y}^{obs}\right)^2} \quad (7)$$

$$RMSECV = \sqrt{\frac{\sum_{i=1}^{n}\left(y_i^{obs} - y_i^{predcv}\right)^2}{n}} \quad (8)$$

In the formulas, $y_i^{obs}$ represents a measured value of toxicity of the ith compound, $y_i^{predcv}$ represents a predicted value of the toxicity of the ith compound, $\bar{y}^{obs}$ represents a mean of toxicity of a training set, and n represents the number of compounds in the training set.

Further, in the step f above, a calculation formula of the leverage value $h_i$ is:

$$h_i = x_i^T (X^T X)^{-1} x_i \qquad (9)$$

In the formula, $x_i$ represents a column vector composed of structural parameters of the ith metal; for a double-parameter model, $$x_i = \begin{pmatrix} x_{11} \\ x_{12} \end{pmatrix}, \quad X = \begin{pmatrix} x_{11} & x_{12} \\ x_{21} & x_{22} \\ \vdots & \vdots \\ x_{n1} & x_{n2} \end{pmatrix};$$

$X^T$ represents the transposed matrix of the matrix X, and $(X^T X)^{-1}$ represents an inverse matrix of a matrix $X^T X$.

Further, in the step f above, a computational formula of a critical value h* is:

$$h^* = \frac{3(p+1)}{n} \qquad (10)$$

In the formula, p represents a variable number in the model, p is equal to 2 in the double-parameter model, and n represents the number of compounds in a model training set and is determined according to the number of metals in the training set in each QSAR equation after calibration in steps a-e.

an ordinate space of h<h* in the leverage vs residuals diagram is the application domain of the model.

Further, the specific process of the step g above is as follows:

step g1, sequentially obtaining double-parameter QSAR predictive equations of preferred five-phylum and eight-family aquatic organisms according to methods in the steps a-f;

step g2, collecting and sorting values of all structural descriptors of to-be-predicted metals in the eight equations, substituting into the equations to calculate acute toxic endpoints of the to-be-predicted metals on various species;

step g3, sequencing metal toxicity data of each species corresponding to each metal from lowest to highest, and building a species sensitivity distribution diagram by taking accumulated percentages as vertical ordinates; and step g4, fitting curves by adopting a nonlinear Sigmoidal-logistic fitting equation, and calculating corresponding hazard concentrations of $HC_5$, $HC_{10}$ and $HC_{20}$ when the accumulated percentages are 0.05, 0.1 and 0.2 according to the fitting equation.

Compared with the prior art, the present invention has the beneficial effects that: 1, in the prior art, only the toxic endpoint of the single species is predicted, so model prediction is not accurate enough and the prediction error is in about two orders of magnitude; in the present invention, five-phylum and eight-family aquatic species are systematically screened to serve as a minimum biological prediction set based on an ecological principle, for respectively constructing multivariate predictive models, thereby improving precision and prediction capability of the models;

2 Criteria maximum concentrations (CMCs) are predicted by combining the QSAR models and SSD analysis.

In the prior art, toxic endpoint values are obtained through an experimental testing means, and the species sensitivity analysis is performed to further derive a criteria value. In the present patent, toxicity values of multiple metals are predicted through a QSAR model method, which is quick and simple; and prediction of metal criteria with deficiency of multiple toxicity data is completed by depending on fewer testing data.

DETAILED DESCRIPTION OF PREFERRED EMBODIMENTS

The above-mentioned and additional technical features and advantages of the present inventions are described below in detail in combination with drawings.

The principle of the present invention is to predict an unknown toxic endpoint of a metal according to a quantitative relationship between structural characteristics of heavy metal ions and acute toxicity effects of aquatic organisms, and hazard concentrations for protecting the aquatic organisms of 5%, 10% and 20% are derived from sensitivity distribution analysis on different species. The present invention is a method for establishing a QSAR metal toxicity predictive model by integrating physicochemical structural parameters of heavy metals and toxic mechanisms of different aquatic organisms and applying the QSAR metal toxicity predictive model to prediction of an unknown criteria reference value.

Figure 1:
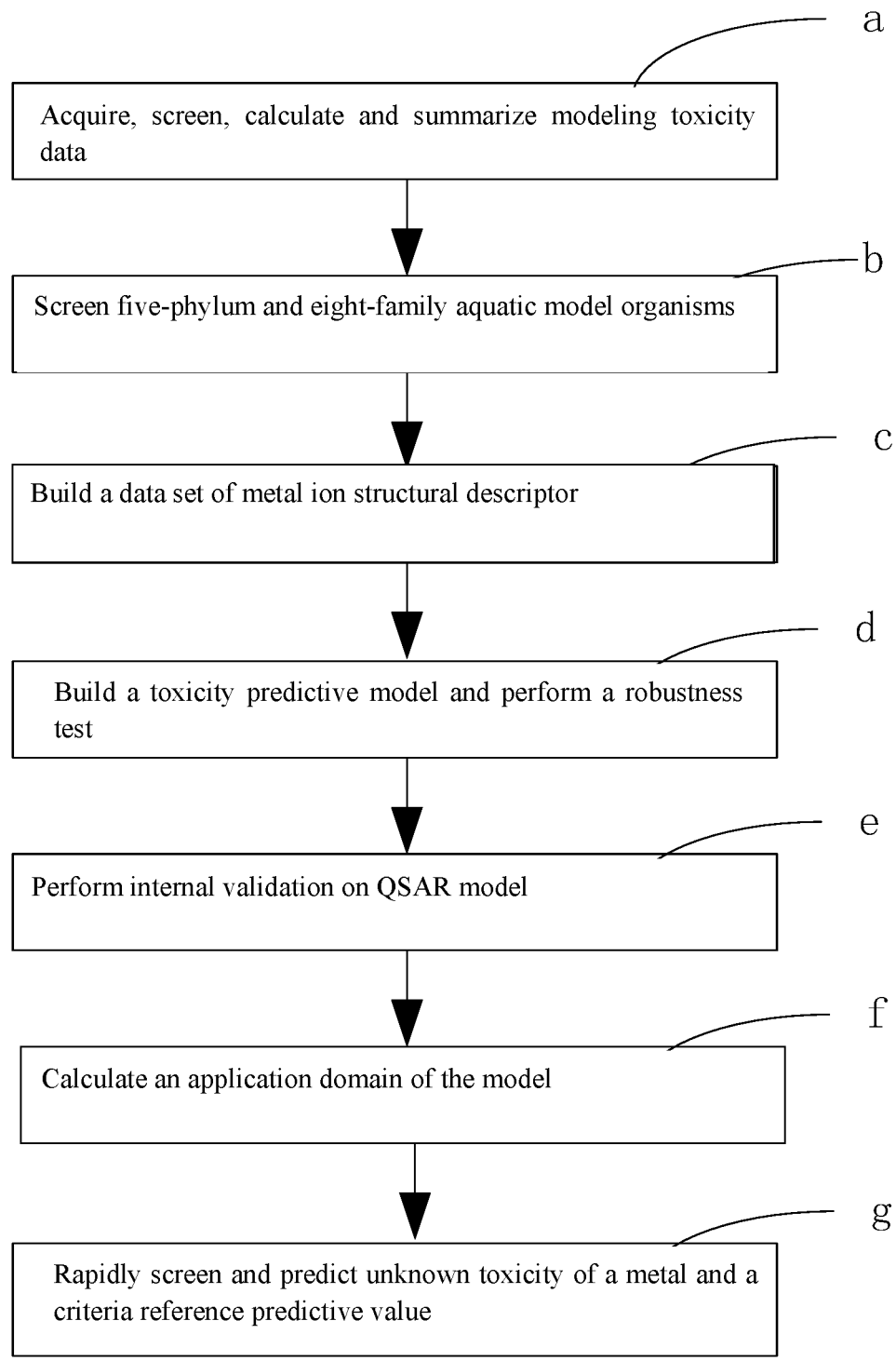
FIG. 1 is a flow chart of a fresh water acute criteria prediction method based on a quantitative structure-activity relationship for metals in the present invention.

FIG. 1 shows a flow chart of a fresh water acute criteria prediction method based on a quantitative structure-activity relationship for metals in the present invention. A specific process is as follows:

step a, acquiring, screening, calculating and summarizing modeling toxicity data;

step a1, a data acquiring process;

step a2, a data screening process, wherein the data screening should meet the following conditions:

1) acute toxicity data of each species must come from the same testing source, the same research group and the same testing conditions;

2) each species comprises the toxicity data of at least 6 metals;

3) types of the toxic endpoint data comprise a fatality rate, a growth rate and a reproductive rate, represented as $EC_{50}$ or $LC_{50}$;

4) a toxicity testing must be performed through standard operation flows under environmental conditions in a certain range; and 5) biological testing exposure time is 48-96 hours;

step a3, a data calculating process, wherein an operational method in embodiments of the present invention is as follows:

by taking free ion concentrations of the metals as data measurement indexes, the unit is obtained by dividing the mass concentration by molecular weight and transforming into a molar concentration in a unified manner, that is, mol/L;

step a4, a data summarizing process:

the finally obtained data set comprises a metallic compound molecular formula, types of tested organisms, types of toxicity effects, endpoint indexes, testing conditions, exposure time and data sources.

A detailed toxicity data acquisition process is as follows:

The modeled acute toxicity data is preferably acquired from a U.S. Environmental Protection Agency ECOTOX toxicity database (http://cfpub.epa.gov/ecotox/). If the toxicity data is deficient, available data (ISI Web of Knowledge) queried by SCI science citation index in recent 30 years is taken as supplementary. By means of a database and a literature search engine, key words such as metal names, names of to-be-tested species, acute toxicity and the like are input to derive toxicity data sets meeting conditions. Qualified toxicity data is screened on premise of meeting the conditions in the step a2. The free ion concentrations of the metals are taken as the measurement indexes of the data, and if original data takes ionic compound mass as a toxic endpoint index, the concentration needs to be divided by the molecular weight and transformed into a micro-molar concentration in a unified manner, that is, μmol/L. In a data compilation process, atomic or molecular formulas of the metals, atomic or molecular weight, endpoint indexes, the types of tested organisms, the testing conditions, the types of toxicity effects, the exposure time, the data sources and other information are recorded and sorted in an Excel form to serve as a modeling basis.

Step b, screening five-phylum and eight-family aquatic model organisms;

for acute model organisms, five-phylum and eight-family organisms for deriving water quality criteria recommended by U.S. Environmental Protection Agency are taken as the base for screening five-phylum and eight-family model organisms sensitive to heavy metals from fresh water, including 3 kinds of plankton crustacean arthropods, 2 kinds of chordates, 1 kind of mollusk, 1 kind of rotifers and 1 kind of duckweeds. For each kind of model organisms, corresponding toxicity data should strictly conform to data acquiring and screening requirements, and acute toxicity data of each species are sequentially summarized. If the number of species meeting the requirements exceeds the minimum species number requirement, organisms with rich tested metal types are selected for modeling. For example, through data acquisition, if five species types in the plankton crustacean arthropods meet the conditions, the species are sorted according to quantity of tested metal elements, and the first three species are selected as the model organisms. Scientific names, belonging categories and families of the eight organisms are determined after the model organisms are screened;

step c, building a data set of metal ion structural descriptors;

the built metal ion structural descriptor set comprises a soft index $\sigma p$, a maximum stability constant log-$\beta_n$ of complexes, Pauling electronegativity $X_m$, a covalence index $X_m^2 r$, an atom ionization potential $AN/\Delta IP$, a first hydrolysis constant $|\log K_{OH}|$, an electrochemical potential $\Delta E_0$, an atomic size AR/AW, polarizable force parameters $Z/r$, $Z/r^2$ and $Z^2/r$ and quasi polarizable force parameters $Z/AR$ and $Z/AR^2$.

step c1, performing linear regression analysis by taking a toxic endpoint of a single species as a dependent variable and taking a structural parameter corresponding to each metal as an independent variable, and calculating a Pearson's correlation coefficient r according to the following formula (1):

$$r = \frac{\sum_{i=1}^{n}(x_i - \bar{x})(y_i - \bar{y})}{\sqrt{\sum_{i=1}^{n}(x_i - \bar{x})^2(y_i - \bar{y})^2}} \quad (1)$$

In the formula, $x_i$ and $y_i$ respectively represent the structural parameter and measured toxicity value corresponding to the ith metal, and $\bar{x}$ and $\bar{y}$ respectively represent the means of each structural parameter and measured toxicity value. The correlation coefficient r>0.8 is a significant correlation parameter. Correlation degree between two factors can be simply and objectively measured by adopting Pearson's correlation.

Step c2, obtaining structural descriptors in the top two by correlation coefficient sorting on the premise of significant correlation, and screening structural parameters in significant correlation with the toxicity through the correlation coefficient r in the step, to prevent spurious correlation parameters from being introduced into the model.

Step d, building a toxicity predictive model and performing a robustness test;

step d1, building a multiple regression equation and estimating parameters.

Two optimal structural parameters determined in the step d above are the independent variable X, a metal activity value is the dependent variable Y, a quantitative ion characteristic-activity correlation equation Y=XB+E of each model organism is constructed by utilizing a multiple linear regression analysis method, and a formula (2) below is referred to, wherein:

$$Y = \begin{pmatrix} y_1 \\ y_2 \\ \vdots \\ y_n \end{pmatrix}, \quad X = \begin{pmatrix} 1 & x_{11} & x_{12} \\ 1 & x_{21} & x_{22} \\ \vdots & \vdots & \vdots \\ 1 & x_{n1} & x_{n2} \end{pmatrix}, \quad B = \begin{pmatrix} \beta_0 \\ \beta_1 \\ \beta_2 \end{pmatrix}, \quad E = \begin{pmatrix} \varepsilon_1 \\ \varepsilon_2 \\ \vdots \\ \varepsilon_n \end{pmatrix} \quad (2)$$

n is the number of observed values; B represents an unknown parameter and needs to be estimated by a least square method in the equation; and E represents a random error term and reflects the influence of random factors on y except for a linear relationship between $x_1$ and $x_2$ on y. Compared with unary linear regression, a relationship between two different structural parameters and the metal toxicity value is established in the equation (2) by adopting multiple linear regression, and a relationship between a prediction object and correlation factors is completely and accurately expressed.

Parameters in the equation are estimated by the least square method, and X' is a transposed matrix of X:

$$\hat{B} = \begin{pmatrix} \hat{\beta}_0 \\ \hat{\beta}_1 \\ \dots \\ \hat{\beta}_m \end{pmatrix} = (X'X)^{-1}X'Y \quad (3)$$

Least square regression is to perform parameter evaluation on a regression model from an error fitting angle, is a standard multiple modeling tool and is particularly applicable to prediction analysis.

Step d2, inspecting goodness of fit and inspecting significance of the regression equation (F-testing):

A testing index of goodness of fit of the model refers to: square ($R^2$) of the correlation coefficient, a degree-of-freedom corrected correlation coefficient ($\overline{R}^2$), and a standard deviation (RMSE). Indexes of F-testing refer to the value F and correlation probability p calculated by Multi-ANOVA. Generally, testing is preformed by adopting the value P corresponding to the statistic F.

Step d3, obtaining a judgment standard: according to a toxicity data acquisition way, in-vitro experiment $R^2$ is more than or equal to 0.81, and in-vivo experiment $R^2$ is more than or equal to 0.64. A significance level is $\alpha$, and when p is less than $\alpha$, the regression equation is significant.

$$R^2 = 1 - \frac{\sum_{i=1}^{n}(y_i - \hat{y})^2}{\sum_{i=1}^{n}(y_i - \overline{y})^2} \quad (4)$$

$$\overline{R}^2 = 1 - (1 - R^2)\frac{n-1}{n-3}$$

$$RMSE = \sqrt{\frac{\sum_{i=1}^{n}(y_i - \hat{y})^2}{n-3}} \quad (5)$$

$$F = \frac{[SS(\text{total}) - SS(\text{residual})]/2}{SS(\text{residual})/(n-3)} = \frac{\left[\sum_{i=1}^{n}(y_i - \overline{y})^2 - (y_i - \hat{y})^2\right](n-3)}{2 \times \sum_{i=1}^{n}(y_i - \hat{y})^2} \quad (6)$$

In the formulas, $y_i$ represents a measured toxicity value of the ith metal, $\hat{y}$ represents a predicted toxicity value of the ith metal, $\overline{y}$ represents the mean of each toxicity value, and n is the number of metals in the training set.

The goodness of fit of a regression line can be measured by the correlation coefficient and the standard deviation in the equations (4) and (5); and an equation (6) is a universal method for inspecting whether a linear relationship between the dependent variable and multiple independent variables is significant.

Step e, performing internal validation on the QSAR model.

The QSAR model of each species should be authenticated by a leave-one-out method. A core thought of the method is to randomly take out a data from the training set, establish a multiple regression model by using other toxicity data and the optimized structural descriptor obtained in the step c and compare a predicted value of the taken-out data and an experimental value to validate the established network model. In order to reduce variability of cross-validation results, a sample data set is divided repeatedly in different ways to obtain different complementary subsets for performing multiple cross-validations. The mean of multiple validations serves as the validation result in the present step.

The internal validation method has the advantage that almost all samples are used for training the model, and the model is closest to the sample, so that the evaluated result is reliable; any random factor does not exist in the experiment, and the whole process is repeatable.

Specific steps are as follows:

step e1, selecting most of the samples for modeling in given modeling samples, reserving a small part of the samples for predicting by using the established model, and calculating prediction errors of the small part of the samples;

step e2, recording the sum of squares of the prediction errors in each equation until all the samples are predicted once only;

step e3, calculating a cross-validation correlation coefficient $Q^2_{cv}$ and a cross-validation root-mean-square error $RMSE_{CV}$, wherein a calculation formula is as follows, and the discrimination basis is that: $Q^2_{cv} > 0.6$ and $R^2 - Q^2_{cv} \leq 0.3$.

$$Q^2_{cv} = 1 - \frac{\sum_{i=1}^{n}(y_i^{obs} - y_i^{predcv})^2}{\sum_{i=1}^{n}(y_i^{obs} - \overline{y}^{obs})^2} \quad (7)$$

$$RMSECV = \sqrt{\frac{\sum_{i=1}^{n}(y_i^{obs} - y_i^{predcv})^2}{n}} \quad (8)$$

In the formulas, $y_i^{obs}$ represents a measured value of toxicity of the ith compound, $y_i^{predcv}$ represents a predicted value of the toxicity of the ith compound, $\overline{y}^{obs}$ represents a mean of toxicity of a training set, and n represents the number of compounds in the training set.

Equations (7) and (8) are indicator parameters of leave-one-out internal validation, overfitting of the model on the training set data can be effectively reduced, and whether a particular metal in the training set influences robustness of the model or not is measured.

Step f, calculating a model application domain.

For a calibrated model, the application domain of the model is calculated by a leverage value method and intuitively represented by a leverage vs residuals diagram. The method may guarantee that the model has optimal reliability in the prediction process.

A calculation formula of a leverage value $h_i$ is as follows:

$$h_i = x_i^T(X^TX)^{-1}x_i \quad (9)$$

In the formula, xi represents a column vector composed of structure parameters of the ith metal; for a double-parameter model, $$Xi = \begin{pmatrix} X_{i1} \\ X_{i2} \end{pmatrix},$$

$$X = \begin{pmatrix} X_{11} & X_{12} \\ X_{21} & X_{22} \\ \vdots & \vdots \\ X_{n1} & X_{n2} \end{pmatrix};$$

XT represents the transposed matrix of the matrix X, and (XTX)-1 represents an inverse matrix of a matrix XTX.

A calculation formula of a critical value h* is as follows:

$$h^* = \frac{3(p+1)}{n} \quad (10)$$

In the formula, p represents a variable number in the model, p is equal to 2 in the double-parameter model, and n represents quantity of compounds in a model training set and is determined according to the number of metals in the training set in each QSAR equation after calibration in steps a-e.

A leverage vs residuals diagram is drawn by taking a leverage value h as a horizontal ordinate and taking a standardized residual of each data point as a vertical coordinate. A coordinate space of h<h* in the diagram is the application domain of the model.

Step g, rapidly screening and predicting the toxicity of an unknown metal and a criteria prediction value by adopting the obtained toxicity prediction value and species sensitivity analysis.

Step g1, sequentially obtaining double-parameter QSAR predictive equations of preferred five-phylum and eight-family aquatic organisms according to methods in the steps a-f;

step g2, collecting and arranging values of all structural descriptors of to-be-predicted metals in the eight equations and substituting into the equations to calculate acute toxic endpoints of the to-be-predicted metals on various species;

step g3, sorting metal toxicity data of each species corresponding to each metal from lowest (the most sensitive species) to highest (the least sensitive species), and building a species sensitivity distribution diagram by taking accumulated percentages as vertical coordinates (P=(R−0.5)/N, R refers to species No., and N refers to species quantity); and step g4, fitting curves (formula) by adopting a nonlinear Sigmoidal-logistic fitting equation, and calculating corresponding hazard concentrations of $HC_5$, $HC_{10}$ and $HC_{20}$ when the accumulated percentages are 0.05, 0.1 and 0.2 according to the fitting equation.

Discrimination indexes of curve goodness of fit comprise $\overline{R}^2$, $$RSS = \sum_{i=1}^{n}(y_i - \overline{y})^2, F \text{ and } P.$$

The calculation method is shown in the equations (4)-(6).

$$y = \frac{a}{1 + e^{-k(x-x_e)}} \quad (11)$$

In the formula, a represents amplitude of the fitted curve, $x_c$ represents a central value, and k represents rate of curve. Many researches prove that the nonlinear Sigmoidal-logistic fitted model has the optimal fitting effect on a species sensitivity curve. Therefore, the method is adopted as a method for deriving the metal criteria prediction value in the present invention.

The present invention is further described below in combination with drawings through embodiments.

Embodiment 1

Acute toxicity data of *Daphnia magna* is summarized by adopting the method in the step a of the present invention, as shown in Table 1.

TABLE 1

Screening, Operating and Summarizing Examples of Acute Toxicity Data

| Metal Type | Endpoint Index | Molecular weight | Endpoint (μmol/L) | Tested oganism | Experimental condition | Effect Type | Exposure Time | Data source |
|---|---|---|---|---|---|---|---|---|
| Mercury | 0.022 | 201 | −0.9608 | *Daphnia magna* | Temperature: 13° C.; pH: 7.6; Dissolved oxygen: 5.6 mg/L; Total hardness: 240 mg/L | Fatality rate | 48 hours | B. S. and P. K. Ray. Ecotoxicology and Environmental Safety. 1989, 18, 109-120 |
| Silver | 0.014 | 108 | −0.8873 | | | | | |
| Copper | 0.014 | 64 | −0.6601 | | | | | |
| Zinc | 0.13 | 65 | 0.3010 | | | | | |
| Lead | 8.69 | 207 | 1.6230 | | | | | |
| Iron | 2.92 | 56 | 1.7172 | | | | | |
| Nickel | 5.7 | 59 | 1.9850 | | | | | |

Embodiment 2

Information of five-phylum and eight-family aquatic organisms is preferred by adopting the method in the step b of the present invention, as shown in Table 2.

TABLE 2

Preferred Acute and Chronic Model Organisms

| Species | Phylum | Family |
|---|---|---|
| Chironomidae | Arthropoda | Chironomidae |
| Opossum shrimp | Arthropoda | Mysidae |
| *Daphnia magna* | Arthropoda | Daphniidae |
| Lymnaea | Mollusca | Lymnaeidae |
| Carp | Chordata | Cyprinidae |
| Rotifer | Rotifer | Brachionidae |
| Toad larvae (tadpole) | Chordata | Bufonidae |
| Duckweed | Angiospermae | Araceae |

Embodiment 3

Toxicity values of metal mercury on eight-family model organisms are predicted by the method in the present invention, and a criteria reference value is predicted by combining the SSDs.

According to the methods in the steps a-d, toxicity predictive equations of the eight-family model organisms are respectively built, as shown in Table 3. Optimized structural parameters of mercury are calculated as follows: $\sigma p=0.065$, $\log\text{-}\beta_n=21.7$, $X_m^2 r=4.08$, $AN/\Delta IP=9.62$, $Z/r=1.96$, $|\log K_{OH}|=3.4$ and $\Delta E_0=0.91$. The parameters are sequentially substituted into the equations to obtain the toxicity prediction value of each species.

TABLE 3

QSAR Toxicity Predictive Equations of Eight-Family Model Organisms

| Species | Predictive equations | $R^2$ | P | Predicted value |
|---|---|---|---|---|
| Chironomidae | $\log 48h\text{-}EC_{50} = (28.136 \pm 18.459) \sigma p + (-0.150 \pm 0.112) \log\text{-}\beta_n + (0.814 \pm 3.625)$ | 0.769 | 0.012 | −0.612 |
| Opossumshrimp | lo $\log 96h\text{-}LC_{50} = (39.716 \pm 25.627) .254 \pm 0.136) \log\text{-}\beta_n + (1.678 \pm 4.533)$ | 0.791 | 0.004 | −1.252 |
| *Daphnia magna* | $\log 48h\text{-}EC_{50} = (-0.272 \pm 18.674) \sigma p + (-0.360 \pm 0.136) \log\text{-}\beta_n + (6.604 \pm 4.093)$ | 0.869 | 0.017 | −1.226 |
| Lymnaea | $\log 96h\text{-}EC_{50} = (-2.160 \pm 0.821) X_m^2 r + (0.237 \pm 0.222) AN/\Delta IP + (5.557 \pm 1.399)$ | 0.827 | 0.070 | −0.976 |
| Carp | $\log 96h\text{-}LC_{50} = (33.439 \pm 6.256) \sigma p + (0.412 \pm 0.137) Z/r + (-3.159 \pm 0.559)$ | 0.960 | 0.008 | −0.178 |
| Rotifer | $\log 24h\text{-}LC_{50} = (-0.297 \pm 0.082) \log\text{-}\beta_n + (-0.111 \pm 0.106) \log K_{OH}| + (6.375 \pm 2.058)$ | 0.823 | 0.070 | −0.447 |
| tadpole | $\log 96h\text{-}LC_{50} = (6.955 \pm 20.353) \sigma p + (-1.569 \pm 0.474) X_m^2 r + (5.014 \pm 3.156)$ | 0.902 | 0.009 | −0.935 |
| Duckweed | $\log 96h\text{-}EC_{50} = (24.984 \pm 9.959) \sigma p + (1.494 \pm 0.439) \Delta E_0 + (-2.046 \pm 1.140)$ | 0.824 | 0.030 | 0.938 |

Embodiment 4

The model is subjected to internal validation by adopting the method in the step e of the present invention. By taking an acute toxicity prediction equation $\log\text{-}EC_{50}=(-0.272\pm18.674)\sigma p+(-0.360\pm0.136)\log\text{-}\beta_n+(6.604\pm4.093)$ of *Daphnia magna* as an example, the model is subjected to leave-one-out internal validation, and correlation fitting parameters are shown in Table 4. $Q^2_{cv}=0.63$, $RMSE_{CV}=1.139$, and $R^2-Q^2_{cv}=0.239$ are calculated according to the formulas (7) and (8) in the step e. If the model robustness discrimination bases $Q^2_{cv}>0.6$ and $R^2-Q^2_{cv}\leq0.3$ are met, the model passes the internal validation.

TABLE 4

Internal Validation Leave-One-Out Correlation Parameters of the Model

| Metals | $\sigma p$ | $\log\text{-}\beta_n$ | Observed value | Coefficient 1 | Coefficient 2 | Intercept | Predicted value |
|---|---|---|---|---|---|---|---|
| Mercury | 0.065 | 20.9 | −0.9608 | −1.2132 | −0.3617 | 6.7468 | −0.8916 |
| Silver | 0.074 | 20.6 | −0.8873 | −0.9165 | −0.3586 | 6.6672 | −0.7878 |
| Copper | 0.104 | 18.5 | −0.6601 | 8.5564 | −0.2874 | 4.5836 | 0.1566 |
| Zinc | 0.115 | 17.66 | 0.3010 | −2.5371 | −0.375 | 7.0789 | 0.1646 |
| Lead | 0.131 | 14.58 | 1.6231 | −6.8774 | −0.3836 | 7.6189 | 1.1251 |
| Iron | 0.103 | 15.77 | 1.7172 | 7.8861 | −0.2894 | 4.4203 | 0.6687 |
| Nickel | 0.126 | 11.33 | 1.9850 | −28.1049 | −0.7115 | 15.7706 | 4.1681 |

Embodiment 5

The model application domain is calculated by adopting the method in the step f of the present invention, and the leverage vs residuals diagram is drawn. By taking an acute toxicity prediction equation $\log\text{-}LC_{50}=(33.439\pm6.256)\sigma p+(0.412\pm0.137)Z/r+(-3.159\pm0.559)$ of carp as an example, structural parameters and toxic endpoints of various metals in the training set are shown in Table 5. The critical value $h^*=3*(2+1)/6$ is equal to 1.5.

TABLE 5

Calculation of Acute Toxicity Prediction Equation Application Domain of Carp

| Type | σp | h(σp) | Z/r | h(Z/r) | Observed value | Predicted value | Residual |
|---|---|---|---|---|---|---|---|
| Copper | 0.104 | 0.174 | 2.7397 | 0.170 | 1.097 | 2.249 | 1.152 |
| Zinc | 0.115 | 0.259 | 2.7027 | 0.172 | 2.079 | 1.800 | −0.279 |
| Nickel | 0.126 | 0.438 | 2.8986 | 0.167 | 2.246 | 1.448 | −0.798 |
| Cadmium | 0.081 | 0.303 | 2.1053 | 0.277 | 0.331 | 0.417 | 0.086 |
| Mercury | 0.065 | 0.638 | 1.9600 | 0.323 | −0.0479 | 0.178 | 0.2259 |
| Chromium | 0.107 | 0.188 | 4.8387 | 0.890 | 2.439 | 2.413 | −0.026 |

Figure 2A:
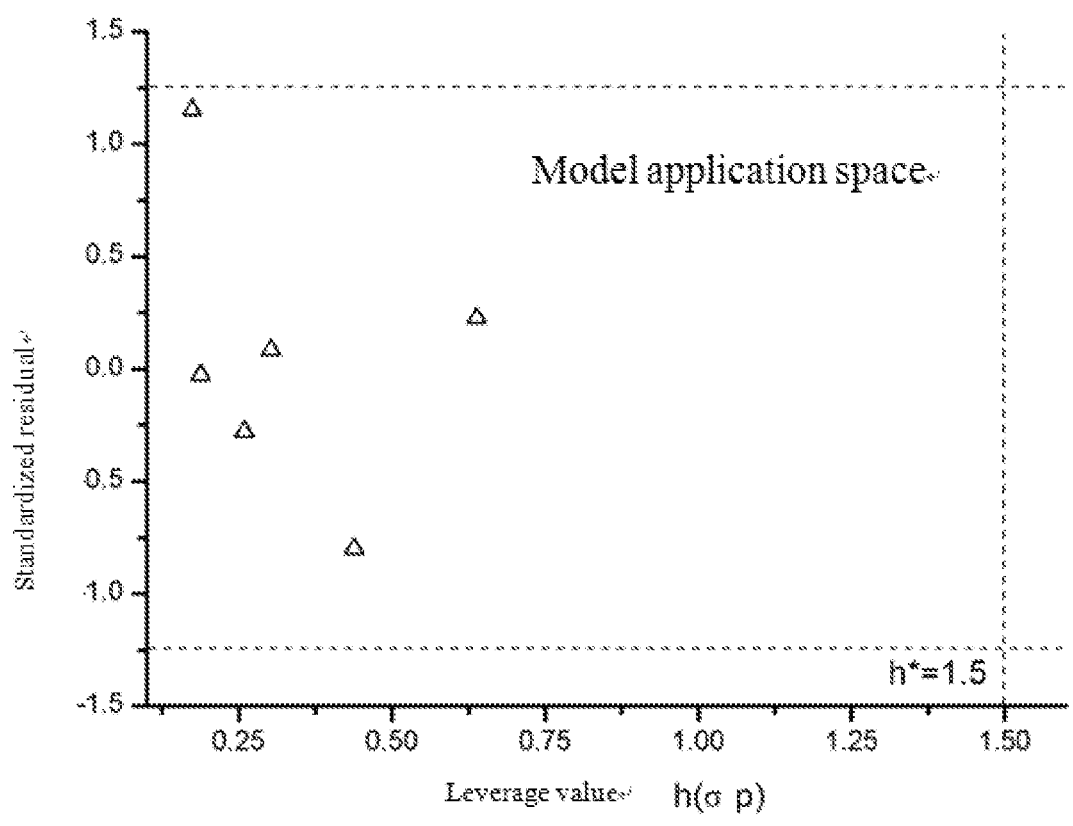
FIG. 2a is a leverage vs residuals diagram I of evaluation of a model application domain in the present invention.
Figure 2B:
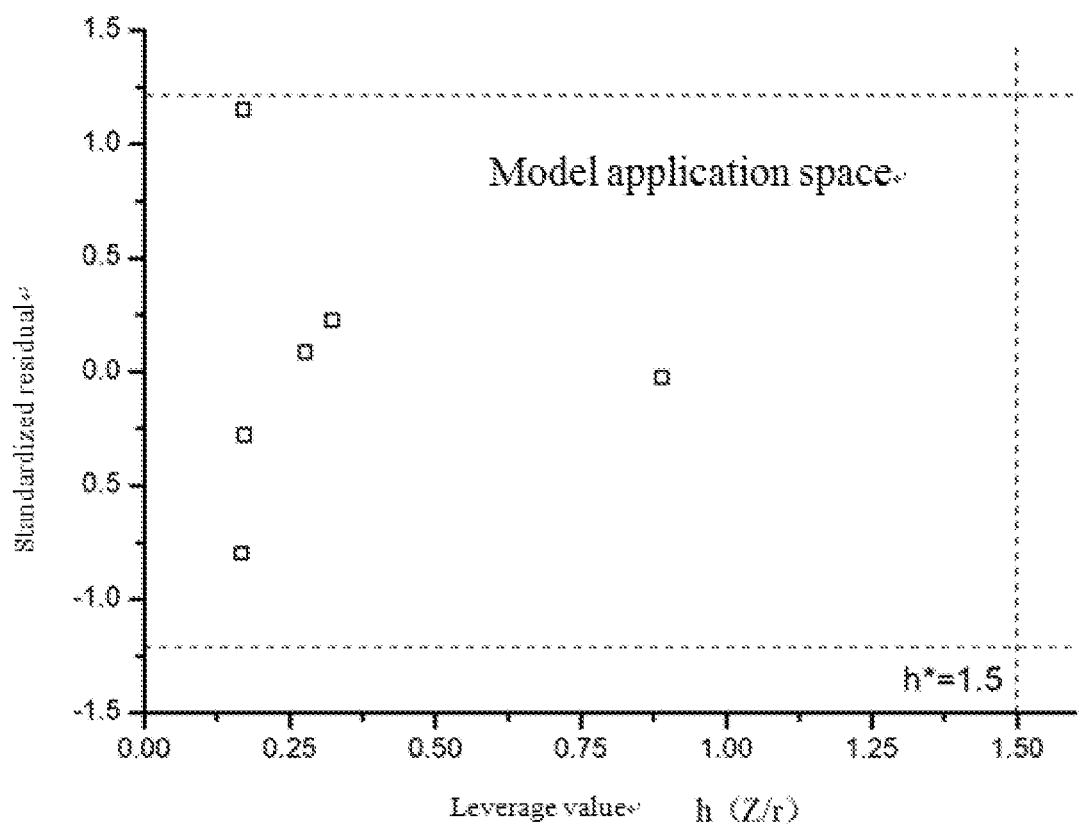
FIG. 2b is a leverage vs residuals diagram II of evaluation of a model application domain in the present invention.

The leverage value of two optimized structural parameters of each metal is taken as the horizontal ordinate, and a predicted residual is taken as the vertical coordinate to draw the leverage vs residuals diagram (FIGS. 2a and b). A space inside three imaginary lines in the figure is the application domain of the model, and the calculation result shows that 6 metals in the training set are included in the prediction range of the model.

Embodiment 6

A QSAR-SSDs curve fitting equation of the metal mercury is obtained according to the step g of the present invention.

$$y = \frac{(0.9273 \pm 0.0593)}{1 + e^{-(3.3526\pm0.5625)[x-(-0.7808\pm0.0647)]}}$$

Figure 3:
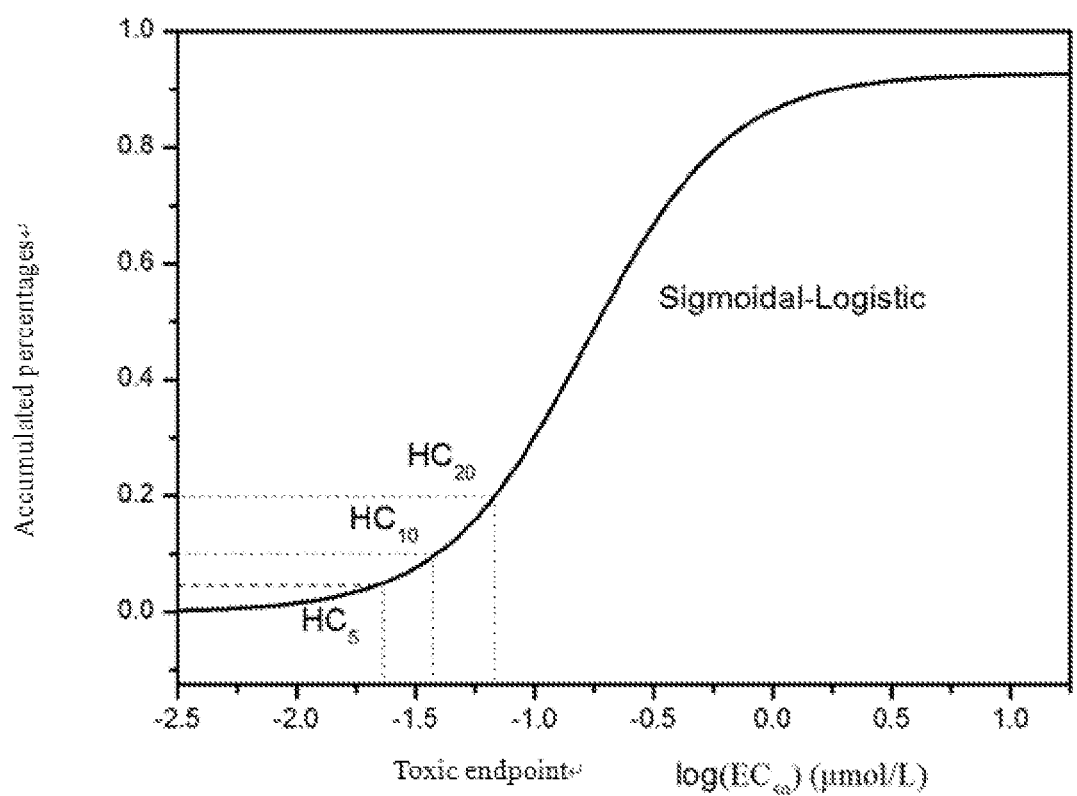
FIG. 3 is a species sensitivity distribution curve of a mercury toxicity predicted value in the present invention.

Various parameters for evaluating the goodness of fit are respectively as follows: $r^2=0.9594$, $RSS=0.019$, $F=231.176$ and $P=1.18\times10^{-5}$. According to the SSDs curve (shown in FIG. 3), when y is equal to 0.05, 0.10 and 0.20, corresponding values of $\log\text{-}HC_5$, $\log\text{-}HC_{10}$ and $\log\text{-}HC_{20}$ are equal to −1.6352, −1.4022 and −1.1658. In a water quality criteria guideline issued by U.S. Environmental Protection Agency in 1985, the hazard concentration of the mercury is derived as −1.8560 based on laboratory determination, and the prediction error is 0.119.

Detailed descriptions above are specific descriptions with respect to one of feasible embodiments of the present invention. The embodiment is not used for limiting patent scope of the present invention. All equivalent implementations or modifications made without deviating from the present invention should be included in the scope of technical solutions of the present invention.

We claim:

1. A fresh water acute criteria prediction method based on a quantitative structure-activity relationship for metals, comprising:
predicting an unknown toxic endpoint of a metal according to a quantitative relationship between structural characteristics of heavy metal ions and acute toxicity effects of aquatic organisms, and hazard concentrations for protecting the aquatic organisms of different proportions are derived from sensitivity distribution analysis on different species;

a specific process is as follows:

step a, acquiring, screening, calculating and summarizing modeling toxicity data;

step b, screening five-phylum and eight-family aquatic model organisms;

step c, building a data set of metal ion's structural descriptors, and performing linear regression analysis between each structural parameter as an independent variable and toxic endpoints, to obtain structural descriptors in the top two by virtue of correlation coefficient sorting;

step d, building a metal toxicity predictive model and performing a robustness test, establishing a multiple regression equation, estimating parameters, and inspecting by adopting a value P corresponding to statistic F;

step e, performing internal validation on a quantitative structure-activity relationship (QSAR) model;

step f, calculating an application domain of the model; and for a calibrated model, drawing a leverage vs residuals diagram by taking a leverage value h as a horizontal ordinate and taking a standardized residual of each data point as a vertical ordinate; and step g, screening and predicting an unknown toxicity of a metal and a criteria value by adopting the obtained toxicity prediction value and species sensitivity analysis.

2. The fresh water acute criteria prediction method based on the quantitative structure-activity relationship for metals according to claim 1, wherein in the step c above, linear regression analysis is performed by taking a toxic endpoint of a single species as a dependent variable and taking the structural parameter corresponding to each metal as the independent variable, and a correlation coefficient r is calculated according to the following formula (1):

$$r = \frac{\sum_{i=1}^{n}(x_i-\bar{x})(y_i-\bar{y})}{\sqrt{\sum_{i=1}^{n}(x_i-\bar{x})^2(y_i-\bar{y})^2}} \tag{1}$$

in the formula, $\bar{x}$ and $\bar{y}$ respectively represent the means of each structural parameter and the toxicity value, and $x_i$ and $y_i$ represent a structural parameter and a toxicity value of the ith metal, respectively; and the correlation coefficient $r>0.8$ is a significant correlation parameter.

3. The fresh water acute criteria prediction method based on the quantitative structure-activity relationship for metals according to claim 2, wherein in the step c above, the built metal ion structural descriptor set comprises a soft index σp, a maximum stability constant $\log\text{-}\beta_n$ of complexes, Pauling electronegativity $X_m$, covalent index $X_m^2 r$, an atom ionization potential $AN/\Delta IP$, a first hydrolysis constant $|\log K_{OH}|$, an electrochemical potential $\Delta E_0$, an atomic size $AR/AW$, polarizable force parameters $Z/r$, $Z/r^2$ and $Z^2/r$ and quasi polarizable force parameters $Z/AR$ and $Z/AR^2$.

4. The fresh water acute criteria prediction method based on the quantitative structure-activity relationship for metals according to claim 2, wherein the process of the step d is as follows:

step d1, building the multiple regression equation and performing parameter estimation;

a quantitative ion characteristic-activity relationship equation Y=XB+E of each model organism is constructed by taking two optimal structural parameters determined in the step d above as the independent variable X and taking a metal activity value as the dependent variable Y through a multiple linear regression analysis method; and a formula (2) below can be referred to, wherein $$Y = \begin{pmatrix} y_1 \\ y_2 \\ \vdots \\ y_n \end{pmatrix}, \quad (2)$$

$$X = \begin{pmatrix} 1 & X_{11} & X_{12} \\ 1 & X_{21} & X_{22} \\ \vdots & \vdots & \vdots \\ 1 & X_{n1} & X_{n2} \end{pmatrix},$$

$$B = \begin{pmatrix} \beta_0 \\ \beta_1 \\ \beta_2 \end{pmatrix},$$

$$E = \begin{pmatrix} \varepsilon_1 \\ \varepsilon_2 \\ \vdots \\ \varepsilon_n \end{pmatrix}$$

n is the number of observed values, B is a regression coefficient matrix, and E is a random error matrix;

parameters in the equation are estimated by a least square method, and X' is a transposed matrix of X:

$$\hat{B} = \begin{pmatrix} \hat{\beta}_0 \\ \hat{\beta}_1 \\ \dots \\ \hat{\beta}_m \end{pmatrix} = (X'X)^{-1}X'Y \quad (3)$$

step d2, inspecting goodness of fit and inspecting significance of the regression equation by adopting F;

a testing index of goodness of fit of the model refers to: square $R^2$ of the correlation coefficient, a degree-of-freedom corrected correlation coefficient $\overline{R}^2$, and a standard deviation RMSE;

indexes of F-testing refer to the value F and correlative probability p calculated by Multi-ANOVA; and testing is preformed by adopting the value P corresponding to the statistic F; and step d3, obtaining a judgment standard: according to a toxicity data acquisition way, in-vitro experiment $R^2$ is more than or equal to 0.81, in-vivo experiment $R^2$ is more than or equal to 0.64; a significance level is α, and when p is less than α, the regression equation is significant.

5. The fresh water acute criteria prediction method based on the quantitative structure-activity relationship for metals according to claim 4, wherein the step d3 above is calculated according to the following formulas:

$$R^2 = 1 - \frac{\sum_{i=1}^{n}(y_i - \hat{y})^2}{\sum_{i=1}^{n}(y_i - \overline{y})^2} \quad (4)$$

$$\overline{R^2} = 1 - (1 - R^2)\frac{n-1}{n-3}$$

$$RMSE = \sqrt{\frac{\sum_{i=1}^{n}(y_i - \hat{y})^2}{n-3}} \quad (5)$$

$$F = \frac{[SS(\text{total}) - SS(\text{residual})]/2}{SS(\text{residual})/(n-3)} = \frac{\left[\sum_{i=1}^{n}(y_i - \overline{y})^2 - (y_i - \hat{y})^2\right](n-3)}{2 \times \sum_{i=1}^{n}(y_i - \hat{y})^2} \quad (6)$$

in the formulas, ŷ represents a predicted toxicity value of the ith metal, $R^2$ represents the square of the correlation coefficient, $\overline{R}^2$ represents the degree-of-freedom corrected correlation coefficient, and RMSE represents the standard deviation.

6. The fresh water acute criteria prediction method based on the quantitative structure-activity relationship for metals according to claim 1, wherein the specific process of the step e above is as follows:

step e1, selecting most of samples for modeling in given modeling samples, reserving a small part of samples for predicting by using the established model, and calculating prediction errors of the small part of samples;

step e2, recording the sum of squares of the prediction errors in all the equations until all the samples are predicted once only; and step e3, calculating a cross-validation correlation coefficient $Q^2_{cv}$ and a cross-validation root-mean-square error $RMSE_{CV}$, wherein a discrimination basis is as follows: $Q^2_{cv} > 0.6$ and $R^2 - Q^2_{cv} \leq 0.3$.

7. The fresh water acute criteria prediction method based on the quantitative structure-activity relationship for metals according to claim 6, wherein calculation formulas adopted in the step e3 above are as follows:

$$Q^2_{cv} = 1 - \frac{\sum_{i=1}^{n}(y_i^{obs} - y_i^{predcv})^2}{\sum_{i=1}^{n}(y_i^{obs} - \overline{y}^{obs})^2} \quad (7)$$

$$RMSECV = \sqrt{\frac{\sum_{i=1}^{n}(y_i^{obs} - y_i^{predcv})^2}{n}} \quad (8)$$

in the formulas, $y_i^{obs}$ represents a measured value of toxicity of the ith compound, $y_i^{predcv}$ represents a predicted value of the toxicity of the ith compound, $\overline{y}^{obs}$ represents a mean of toxicity of a training set, and n represents the number of compounds in the training set.

8. The fresh water acute criteria prediction method based on the quantitative structure-activity relationship for metals according to claim 1, wherein in the step f above, a calculation formula of the leverage value $h_i$ is:

$$h_i = x_i^T (X^T X)^{-1} x_i \quad (9)$$

in the formula, $x_i$ represents a column vector composed of structural parameters of the ith metal; for a double-parameter model, $$Xi = \begin{pmatrix} X_{i1} \\ X_{i2} \end{pmatrix},$$

$$X = \begin{pmatrix} X_{11} & X_{12} \\ X_{21} & X_{22} \\ \vdots & \vdots \\ X_{n1} & X_{n2} \end{pmatrix};$$

$X^T$ represents the transposed matrix of the matrix X, and $(X^T X)^{-1}$ represents an inverse matrix of a matrix $X^T X$.

9. The fresh water acute criteria prediction method based on the quantitative structure-activity relationship for metals according to claim 8, wherein in the step f above, a computational formula of a critical value h* is:

$$h^* = \frac{3(p+1)}{n} \quad (10)$$

in the formula, p represents a variable number in the model, p is equal to 2 in the double-parameter model, and n represents the number of compounds in a model training set and is determined according to the number of metals in the training set in each QSAR equation after calibration in steps a-e; and an ordinate space of h<h* in the leverage vs residuals diagram is the application domain of the model.

10. The fresh water acute criteria prediction method based on the quantitative structure-activity relationship for metals according to claim 1, wherein the specific process of the step g above is as follows:

step g1, sequentially obtaining double-parameter QSAR predictive equations of preferred five-phylum and eight-family aquatic organisms according to methods in the steps a-f;

step g2, collecting and sorting values of all structural descriptors of to-be-predicted metals in the eight equations, substituting into the equations to calculate acute toxic endpoints of the to-be-predicted metals on various species;

step g3, sequencing metal toxicity data of each species corresponding to each metal from lowest to highest, and building a species sensitivity distribution diagram by taking accumulated percentages as vertical ordinates; and step g4, fitting curves by adopting a nonlinear Sigmoidal-logistic fitting equation, and calculating corresponding hazard concentrations of $HC_5$, $HC_{10}$ and $HC_{20}$ when the accumulated percentages are 0.05, 0.1 and 0.2 according to the fitting equation.

* * * * *